United States Patent [19]

Keil et al.

[11] Patent Number: 4,867,784
[45] Date of Patent: Sep. 19, 1989

[54] CYCLOHEXENONE DERIVATIVES, PREPARATION THEREOF AND USE THEREOF AS HERBICIDAL AND PLANT GROWTH REGULATOR AGENTS

[75] Inventors: Michael Keil, Freinsheim; Wolfgang Spiegler, Worms; Dieter Jahn, Edingen-Neckarhausen; Dieter Kolassa, Ludwigshafen; Ulrich Schirmer, Heidelberg; Bruno Wuerzer, Otterstadt; Norbert Meyer, Ladenburg; Wilhelm Rademacher; Johann Jung, both of Limburgerhof, all of Fed. Rep. of Germany

[73] Assignee: BASF Aktiengesellschaft, Ludwigshafen, Fed. Rep. of Germany

[21] Appl. No.: 3,147

[22] Filed: Jan. 14, 1987

[30] Foreign Application Priority Data

Jan. 18, 1986 [DE] Fed. Rep. of Germany ....... 3601368

[51] Int. Cl.$^4$ ............................................. A01N 31/04
[52] U.S. Cl. ........................................ 71/98; 564/256; 564/340; 568/29; 568/31; 568/43; 71/103
[58] Field of Search .................. 564/256, 340; 568/31, 568/29, 43; 71/103, 50, 98

[56] References Cited

U.S. PATENT DOCUMENTS

| 4,249,937 | 2/1981 | Iwataki et al. | 71/98 |
| 4,515,729 | 5/1985 | Iwataki et al. | 71/98 |
| 4,517,013 | 5/1985 | Becker et al. | 71/98 |
| 4,579,971 | 4/1986 | Iwataki et al. | 71/98 |

FOREIGN PATENT DOCUMENTS

| 3227332 | 1/1984 | Fed. Rep. of Germany | 71/103 |
| 3227389 | 1/1984 | Fed. Rep. of Germany | 71/103 |

Primary Examiner—James H. Reamer
Attorney, Agent, or Firm—Keil & Weinkauf

[57] ABSTRACT

Cyclohexenone derivatives of the formula

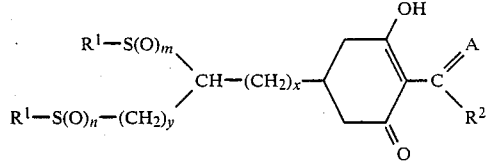

where $R^1$, $R^2$, A, m, n, x and y have the meanings given in the disclosure, a process for their manufacture, herbicidal and plant growth-regulating agents containing the novel active ingredients, and processes for combating unwanted plant growth and for regulating plant growth.

8 Claims, No Drawings

CYCLOHEXENONE DERIVATIVES, PREPARATION THEREOF AND USE THEREOF AS HERBICIDAL AND PLANT GROWTH REGULATOR AGENTS

The present invention relates to novel cyclohexenone derivatives, to processes for their preparation, to herbicidal and plant growth regulator agents which contain the novel active substances and to processes for combating undesirable plant growth and for regulating plant growth.

The herbicidal action of 3-hydroxycyclohex-2-en-1-one derivatives having alkylthioalkyl substituents in the 5-position is known (DE-A-2,822,304 and DE-A-3,227,389). Similar derivatives with alkyl radicals in the 5-position which have two sulfur atoms in any desired position are described in DE-A-3,227,332.

It is further known that certain 2-acyl-3-hydroxycyclohex-2-en-1-ones have a regulating action on plant growth (EP-A-123,001, EP-A-126,713).

We have now found novel cyclohexenone derivatives of the formula I

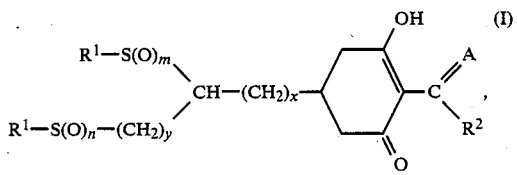

in which
$R^1$ is $C_1$–$C_{18}$-alkyl, $C_3$–$C_6$-alkoxyalkyl, $C_3$–$C_6$-alkylthioalkyl, $C_3$–$C_6$-dialkylaminoalkyl, $C_3$–$C_6$-alkenyl or $C_3$–$C_6$- alkynyl,
$R^2$ is $C_1$–$C_4$-alkyl,
A is oxygen or $NOR^3$ where $R^3$ is $C_1$–$C_4$-alkyl, $C_3$–$C_4$-alkenyl, $C_3$–$C_4$-alkynyl, $C_2$–$C_4$-haloalkyl, $C_2$–$C_4$-haloalkenyl or $C_2$–$C_4$-alkoxyalkyl,
m and n are identical or different and each is independently of the other 0, 1 or 2 and
x and y are identical or different and each is independently of the other 0 or 1,
and also salts of these compounds.

Cyclohexenone derivatives of the formula I in which A is $NOR^3$ have an advantageous herbicidal activity, preferably against species from the family of the grasses (Gramineae).

Those cyclohexenone derivatives of the formula I in which A is oxygen as well as salts of these compounds exhibit advantageous growth regulating properties and a high level of toleration by plants.

The compounds of the formula I can exist in a plurality of tautomeric forms which are all covered by the claim. For example, the compounds where A is $NOR_3$ can have inter alia the following tautomeric structural elements:

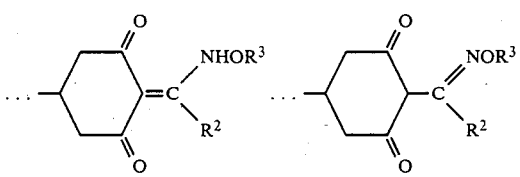

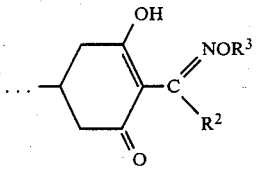

The alkyl groups mentioned in the definitions of $R^1$, $R^2$ and $R^3$ can each be straight-chain or branched.

A $C_2$–$C_4$-haloalkyl or -alkenyl $R^3$ has 1, 2 or 3 halogen atoms. Furthermore, in the case of $C_3$–$C_4$-alkenyl or $C_2$–$C_4$-haloalkenyl $R^3$ radicals where E-and Z-isomers can exist, both the isomers are covered by the claim.

$R^1$ in the formula I is, for example, methyl, ethyl, propyl, isopropyl, butyl, isobutyl, tert-butyl, pentyl, 2-methylbutyl, hexyl, 2-methylpentyl, heptyl, octyl, 2-ethylhexyl, isooctyl, nonyl, isononyl, decyl, isodecyl, 3,5,5,7-tetramethylnonyl, isotridecyl, pentadecyl, hexadecyl, octadecyl, 2-methoxyethyl, 2-ethoxyethyl, 3-methoxypropyl, 2-ethoxybutyl, 2-ethylthioethyl, 2-ethylthiopropyl, 2-(dimethylamino)ethyl, allyl, (E)-but-2-en-1-yl, 2-methyl-isoprop-2-en-1-yl or propargyl. (The names isooctyl, isononyl, isodecyl and isotridecyl are trivial names which derive from the alcohols obtained in the oxosynthesis (cf. Ullmann, Enzyklopadie der Technischen Chemie, 4th edition, volume 7, pages 216 and 217 and volume 11, pages 435 and 436).)

$R^2$ in the formula I is, for example, methyl, ethyl, propyl, isopropyl, butyl, sec-butyl, isobutyl or tert-butyl.

If in the formula I A is $NOR^3$, $R^3$ is, for example, methyl, ethyl, propyl, allyl, (E)-but-2-en-1-yl, propargyl, 2-fluoroethyl, 2-chloroethyl, (E)-1-chloroprop-1-en-3-yl, 1,1,2-trichloroprop-1-en-3-yl, methoxymethyl or methoxyethyl.

Preference is given to cyclohexenone derivatives of the formula I in which $R^1$ is ethyl, $R^2$ is ethyl or propyl, A is oxygen or $NOR^3$ where $R^3$ is ethyl, and m, n, x and y are each O.

Suitable salts of compounds of the formula I are agriculturally utilizable salts, for example the alkali metal salts, in particular the potassium or sodium salts, alkaline earth metal salts, in particular calcium and magnesium salts, manganese, copper, zinc or iron salts and also ammonium, sulfonium, sulfoxonium and phosphonium salts, for example ammonium, tertraalkylammonium, benzyltrialkylammonium, trialkylsulfonium or trialkylsulfoxonium salts.

The cyclohexenone derivatives of the formula I in which A is $NOR^3$ can be advantageously obtained by reacting cyclohexenone derivatives of the formula I in which A is oxygen with an ammonium compound of the formula $R^3O$-$NH_3Y$, where $R^3$ has the abovementioned meanings and Y is an anion, for example a halide, such as fluoride, chloride, bromide or iodide, carbonate or sulfate.

The reaction with the ammonium compound is expediently carried out in heterogeneous phase in an inert diluent at a temperature of from 0° to 80° C. or from 0° C. to the boiling point of the reaction mixture in the presence of a base. Suitable bases are, for example, the carbonates, hydrogencarbonates, acetates, alkanolates, hydroxides or oxides of alkali or alkaline earth metals, in particular of sodium, potassium, magensium or calcium. It is also possible to use organic bases, such as pyridine or tertiary amines.

Examples of inert diluents for this reaction step are dimethyl sulfoxide, alcohols, such as methanol, ethanol or isopropanol, chlorinated or unchlorinated hydrocarbons, such as chloroform, dichloroethane, hexane, cyclohexane, benzene or toluene, carboxylic acid esters, such as ethyl acetate, and ethers, such as dioxane or tetrahydrofuran.

The reaction is complete within a few hours. The reaction product can then be isolated by concentrating the mixture, adding water, extraction with an apolar solvent, such as methylene chloride, and distilling off the solvent under reduced pressure.

Instead of an ammonium compound, the compounds of the formula I (where A is oxygen) can also be reacted with a hydroxylamine of the formula $R^3O-NH_2$, where $R^3$ has the abovementioned meanings, in an inert diluent at a temperature of from 0° C. to the boiling point of the reaction mixture, in particular from 15 to 70° C. If desired, the hydroxylamine can be used in the form of an aqueous solution. Depending on the solvent used for the other reactants, a one- or two-phase reaction mixture is obtained.

Suitable solvents for this reaction are, for example alcohols, such as methanol, ethanol, isopropanol or cyclohexanol, chlorinated or unchlorinated hydrocarbons, such as hexane, cyclohexane, methylene chloride, toluene or dichloroethane, carboxylic acid esters, such as ethyl acetate, nitriles, such as acetonitrile, or cyclic ethers, such as tetrahydrofuran.

The abovementioned alkali metal salts of the cyclohexenone derivatives of the formula I can be obtained by treating these compounds with sodium hydroxide or potassium hydroxide in aqueous solution or in an organic solvent, such as methanol, ethanol or acetone. The base used can also be a sodium or potassium alkanolate.

The other metal salts, for example the manganese, copper, zinc, iron, calcium and magnesium salts, can be prepared from the sodium salts by reaction with the corresponding metal chlorides in aqueous solution. The ammonium, sulfonium, sulfoxonium and phosphonium salts can be prepared from the novel compounds of the formula I by means of ammonium hydroxide, sulfonium hydroxide, sulfoxonium hydroxide or phosphonium hydroxide, if desired in aqueous solution.

The novel cyclohexenone derivatives of the formula I (where A is oxygen) are obtained by reacting a cyclohexanedione derivative of the formula II

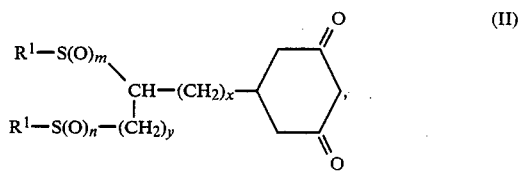

where $R^1$, m, n, x and y have the abovementioned meanings, with an acid chloride of the formula $R^2$-COCl, where $R^2$ has the abovementioned meaning, in an inert solvent (for example tetrahydrofuran) in the presence of a base (for example triethylamine) and subsequently treating the product with an imidazole or pyridine compound (for example 4-(N,N-dimethylamino)pyridine).

A procedure of this kind is known per se and described in JP-A-63,052/1979.

But is also possible to employ other synthetic methods known per se, for example those described in Tetrahedron Lett. 29 (1975), 2491.

The compounds of the formula II are likewise obtained by literature methods, as revealed in the following scheme:

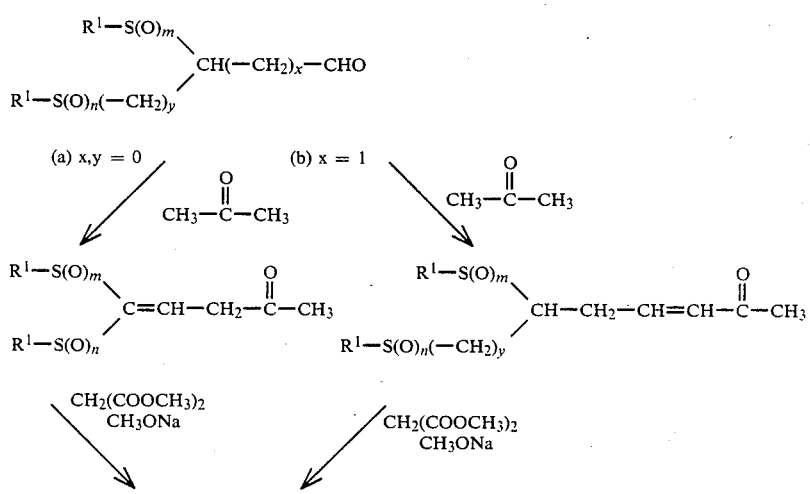

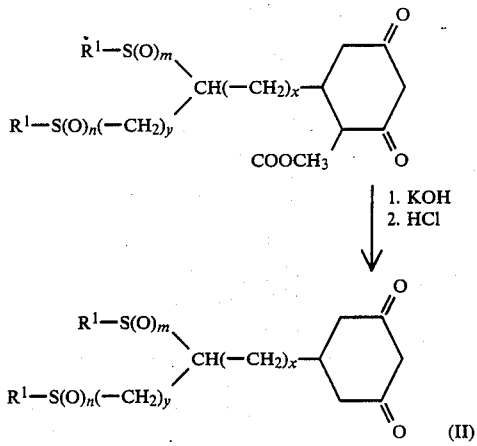

1. KOH
2. HCl

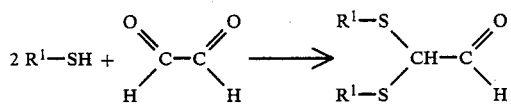

The aldehydes required as starting compounds can be prepared for example by the following methods:

Method A:

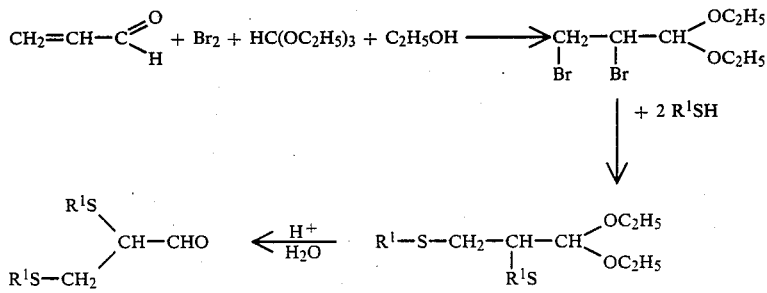

Method B:

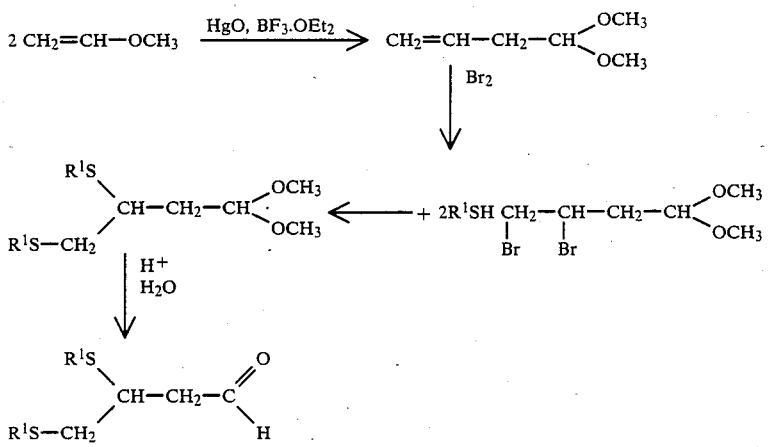

Method C:

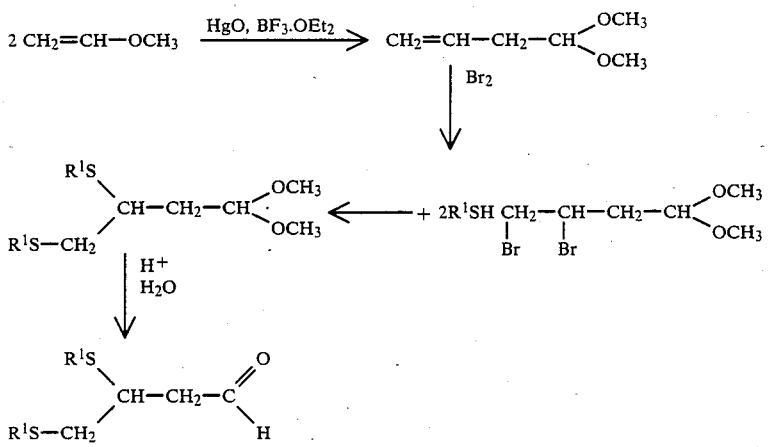

Those compounds of the formula I where m and n are each 1 or 2 can also be obtained by oxidizing the corresponding precursors in which the sulfur is in a lower state of oxidation (m, n =0). Oxidizing agents are, for example, oxygen, ozone, compounds of peroxide structure, for example hydrogen peroxide, peracids or hydroperoxides), halogens, inorganic halogen compounds (for example hypochlorite or chlorate), nitrogen compounds (for example nitric acid or dinitrogen pentoxide) or salts of metals of higher valences (for example lead, bismuth, vanadium, manganese, chromium or cobalt salts). Anodic oxidation is likewise possible. The oxidation can be carried out not only at the final stage (ie. on compounds of formula I), but in principle at any stage of the synthetic pathway described above.

The examples below illustrate the invention in more detail.

EXAMPLE 1

2.4 g of 2-butyryl-5-[bis(ethylthio)methyl]-3-hydroxycyclohex-2-en-1-one, 0.74 g of ethoxyammonium chloride, 0.64 g of sodium hydrogencarbonate and 30 ml of methanol were stirred at room temperature for 16 hours. The solvent was distilled off under reduced pressure, and 50 ml each of water and dichloromethane were added to the residue. After vigorous stirring the phases were separated and the organic phase was dried over sodium sulfate. Distilling off the solvent under reduced pressure left 2.3 g of 5-[bis(ethylthio)methyl]-2-(1-ethoxy-iminobutyl)-3-hydroxy-cyclohex-2-en-1-one as an oil.

The compounds in Tables 1 to 4 below can be obtained in a similar manner or in accordance with one of the methods cited in the description.

TABLE 1

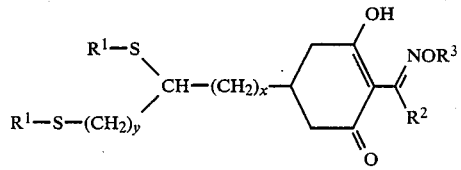

| Compound no. | $R^1$ | $R^2$ | $R^3$ | x | y |
|---|---|---|---|---|---|
| 1 | methyl | ethyl | ethyl | 0 | 0 |
| 2 | methyl | ethyl | ethyl | 0 | 1 |
| 3 | methyl | ethyl | ethyl | 1 | 0 |
| 4 | methyl | ethyl | ethyl | 1 | 1 |
| 5 | methyl | ethyl | allyl | 0 | 0 |
| 6 | methyl | ethyl | allyl | 0 | 1 |
| 7 | methyl | ethyl | allyl | 1 | 0 |
| 8 | methyl | ethyl | allyl | 1 | 1 |
| 9 | methyl | ethyl | (E)—but-2-en-1-yl | 0 | 0 |
| 10 | methyl | ethyl | (E)—but-2-en-1-yl | 0 | 1 |
| 11 | methyl | ethyl | (E)—but-2-en-1-yl | 1 | 0 |
| 12 | methyl | ethyl | (E)—but-2-en-1-yl | 1 | 1 |
| 13 | methyl | ethyl | (E)—1-chloroprop-1-en-3-yl | 0 | 0 |
| 14 | methyl | ethyl | (E)—1-chloroprop-1-en-3-yl | 0 | 1 |
| 15 | methyl | ethyl | (E)—1-chloroprop-1-en-3-yl | 1 | 0 |
| 16 | methyl | ethyl | (E)—1-chloroprop-1-en-3-yl | 1 | 1 |
| 17 | methyl | ethyl | propargyl | 0 | 0 |
| 18 | methyl | ethyl | 2-fluoroethyl | 0 | 0 |
| 19 | methyl | ethyl | methoxymethyl | 0 | 0 |
| 20 | methyl | n-propyl | ethyl | 0 | 0 |
| 21 | methyl | n-propyl | ethyl | 0 | 1 |
| 22 | methyl | n-propyl | ethyl | 1 | 0 |
| 23 | methyl | n-propyl | ethyl | 1 | 1 |
| 24 | methyl | n-propyl | n-propyl | 0 | 0 |
| 25 | methyl | n-propyl | n-propyl | 1 | 1 |
| 26 | methyl | n-propyl | allyl | 0 | 0 |
| 27 | methyl | n-propyl | allyl | 1 | 1 |
| 28 | methyl | n-propyl | (E)—but-2-en-1-yl | 0 | 0 |
| 29 | methyl | n-propyl | (E)—but-2-en-1-yl | 0 | 1 |
| 30 | methyl | n-propyl | (E)—but-2-en-1-yl | 1 | 0 |
| 31 | methyl | n-propyl | (E)—but-2-en-1-yl | 1 | 1 |
| 32 | methyl | n-propyl | (E)—1-chloroprop-1-en-3-yl | 0 | 0 |
| 33 | methyl | n-propyl | (E)—1-chloroprop-1-en-3-yl | 0 | 1 |
| 34 | methyl | n-propyl | (E)—1-chloroprop-1-en-3-yl | 1 | 0 |
| 35 | methyl | n-propyl | (E)—1-chloroprop-1-en-3-yl | 1 | 1 |
| 36 | methyl | n-propyl | 1,1,2-trichloroprop-1-en-3-yl | 0 | 0 |
| 37 | ethyl | methyl | ethyl | 0 | 0 |
| 38 | ethyl | methyl | ethyl | 1 | 1 |
| 39 | methyl | n-propyl | propargyl | 0 | 0 |
| 40 | ethyl | ethyl | ethyl | 0 | 0 |
| 41 | ethyl | ethyl | ethyl | 1 | 1 |
| 42 | ethyl | ethyl | propyl | 0 | 0 |
| 43 | ethyl | ethyl | propyl | 1 | 1 |
| 44 | ethyl | ethyl | allyl | 0 | 0 |
| 45 | ethyl | ethyl | allyl | 0 | 1 |
| 46 | ethyl | ethyl | allyl | 1 | 0 |
| 47 | ethyl | ethyl | allyl | 1 | 1 |
| 48 | ethyl | ethyl | (E)—but-2-en-1-yl | 0 | 0 |
| 49 | ethyl | ethyl | (E)—but-2-en-1-yl | 0 | 1 |
| 50 | ethyl | ethyl | (E)—but-2-en-1-yl | 1 | 0 |
| 51 | ethyl | ethyl | (E)—but-2-en-1-yl | 1 | 1 |
| 52 | ethyl | ethyl | (E)—1-chloroprop-1-en-3-yl | 0 | 0 |
| 53 | ethyl | ethyl | (E)—1-chloroprop-1-en-3-yl | 0 | 1 |
| 54 | ethyl | ethyl | (E)—1-chloroprop-1-en-3-yl | 1 | 0 |
| 55 | ethyl | ethyl | (E)—1-chloroprop-1-en-3-yl | 1 | 1 |
| 56 | ethyl | ethyl | propargyl | 0 | 0 |
| 57 | ethyl | n-propyl | ethyl | 0 | 0 |
| 58 | ethyl | n-propyl | ethyl | 0 | 1 |

TABLE 1-continued

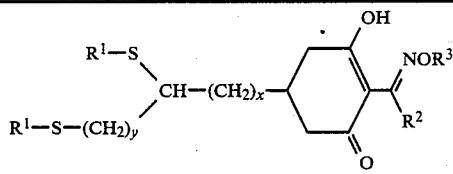

| Compound no. | $R^1$ | $R^2$ | $R^3$ | x | y |
|---|---|---|---|---|---|
| 59 | ethyl | n-propyl | ethyl | 1 | 0 |
| 60 | ethyl | n-propyl | ethyl | 1 | 1 |
| 61 | ethyl | n-propyl | allyl | 0 | 0 |
| 62 | ethyl | n-propyl | allyl | 1 | 1 |
| 351 | ethyl | n-butyl | ethyl | 0 | 0 |
| 63 | ethyl | n-propyl | 2-chloroethyl | 0 | 0 |
| 64 | ethyl | n-propyl | 2-chloroethyl | 1 | 1 |
| 65 | ethyl | n-propyl | 1,1,2-trichloroprop-1-en-3-yl | 0 | 0 |
| 66 | ethyl | n-propyl | methyl | 0 | 0 |
| 67 | ethyl | n-propyl | n-propyl | 0 | 0 |
| 68 | ethyl | n-propyl | n-propyl | 0 | 1 |
| 69 | ethyl | n-propyl | n-propyl | 1 | 0 |
| 70 | ethyl | n-propyl | n-propyl | 1 | 1 |
| 71 | ethyl | n-propyl | (E)—but-2-en-1-yl | 0 | 0 |
| 72 | ethyl | n-propyl | (E)—but-2-en-1-yl | 0 | 1 |
| 73 | ethyl | n-propyl | (E)—but-2-en-1-yl | 1 | 0 |
| 74 | ethyl | n-propyl | (E)—but-2-en-1-yl | 1 | 1 |
| 75 | ethyl | n-propyl | (E)—1-chloroprop-1-en-3-yl | 0 | 0 |
| 76 | ethyl | n-propyl | (E)—1-chloroprop-1-en-3-yl | 0 | 1 |
| 77 | ethyl | n-propyl | (E)—1-chloroprop-1-en-3-yl | 1 | 0 |
| 78 | ethyl | n-propyl | (E)—1-chloroprop-1-en-3-yl | 1 | 1 |
| 79 | ethyl | n-propyl | propargyl | 0 | 0 |
| 80 | ethyl | n-propyl | methoxymethyl | 0 | 0 |
| 81 | n-propyl | ethyl | ethyl | 0 | 0 |
| 82 | n-propyl | ethyl | ethyl | 0 | 1 |
| 83 | n-propyl | ethyl | ethyl | 1 | 0 |
| 84 | n-propyl | ethyl | ethyl | 1 | 1 |
| 85 | n-propyl | ethyl | n-propyl | 0 | 0 |
| 86 | n-propyl | ethyl | n-propyl | 1 | 1 |
| 87 | n-propyl | ethyl | allyl | 0 | 0 |
| 88 | n-propyl | ethyl | allyl | 1 | 1 |
| 89 | n-propyl | ethyl | (E)—but-2-en-1-yl | 0 | 0 |
| 90 | n-propyl | ethyl | (E)—but-2-en-1-yl | 0 | 1 |
| 91 | n-propyl | ethyl | (E)—but-2-en-1-yl | 1 | 0 |
| 92 | n-propyl | ethyl | (E)—but-2-en-1-yl | 1 | 1 |
| 93 | n-propyl | ethyl | (E)—1-chloroprop-1-en-3-yl | 0 | 0 |
| 94 | n-propyl | ethyl | (E)—1-chloroprop-1-en-3-yl | 0 | 1 |
| 95 | n-propyl | ethyl | (E)—1-chloroprop-1-en-3-yl | 1 | 0 |
| 96 | n-propyl | ethyl | (E)—1-chloroprop-1-en-3-yl | 1 | 1 |
| 97 | n-propyl | ethyl | methoxymethyl | 0 | 0 |
| 98 | n-propyl | n-propyl | ethyl | 0 | 0 |
| 99 | n-propyl | n-propyl | ethyl | 0 | 1 |
| 100 | n-propyl | n-propyl | ethyl | 1 | 0 |
| 101 | n-propyl | n-propyl | ethyl | 1 | 1 |
| 102 | n-propyl | n-propyl | allyl | 0 | 0 |
| 103 | n-propyl | n-propyl | allyl | 1 | 1 |
| 104 | n-propyl | n-propyl | (E)—but-2-en-1-yl | 0 | 0 |
| 105 | n-propyl | n-propyl | (E)—but-2-en-1-yl | 1 | 1 |
| 106 | n-propyl | n-propyl | (E)—1-chloroprop-1-en-3-yl | 0 | 0 |
| 107 | n-propyl | n-propyl | (E)—1-chloroprop-1-en-3-yl | 0 | 1 |
| 108 | n-propyl | n-propyl | (E)—1-chloroprop-1-en-3-yl | 1 | 0 |
| 109 | n-propyl | n-propyl | (E)—1-chloroprop-1-en-3-yl | 1 | 1 |
| 110 | n-butyl | ethyl | ethyl | 0 | 0 |
| 111 | n-butyl | ethyl | ethyl | 1 | 1 |
| 112 | n-butyl | ethyl | allyl | 0 | 0 |
| 113 | n-butyl | ethyl | allyl | 1 | 1 |
| 114 | n-butyl | ethyl | n-propyl | 0 | 0 |
| 115 | n-pentyl | ethyl | ethyl | 0 | 0 |
| 116 | n-pentyl | ethyl | ethyl | 1 | 1 |
| 117 | n-pentyl | ethyl | allyl | 0 | 0 |
| 118 | n-pentyl | ethyl | allyl | 1 | 1 |
| 119 | n-pentyl | ethyl | (E)—but-2-en-1-yl | 0 | 0 |
| 120 | n-pentyl | ethyl | (E)—but-2-en-1-yl | 0 | 1 |
| 121 | n-pentyl | ethyl | (E)—but-2-en-1-yl | 1 | 0 |
| 122 | n-pentyl | ethyl | (E)—but-2-en-1-yl | 1 | 1 |
| 123 | n-pentyl | ethyl | (E)—1-chloroprop-1-en-3-yl | 0 | 0 |
| 124 | n-pentyl | ethyl | (E)—1-chloroprop-1-en-3-yl | 0 | 1 |
| 125 | n-pentyl | ethyl | (E)—1-chloroprop-1-en-3-yl | 1 | 0 |
| 126 | n-pentyl | ethyl | (E)—1-chloroprop-1-en-3-yl | 1 | 1 |
| 127 | n-pentyl | n-propyl | ethyl | 0 | 0 |
| 128 | n-pentyl | n-propyl | ethyl | 1 | 1 |

TABLE 1-continued

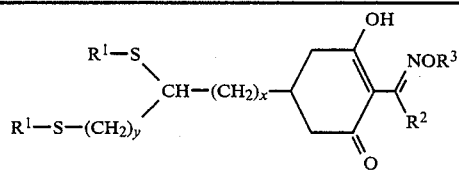

| Compound no. | R¹ | R² | R³ | x | y |
|---|---|---|---|---|---|
| 129 | n-pentyl | n-propyl | allyl | 0 | 0 |
| 130 | n-pentyl | n-propyl | allyl | 1 | 1 |
| 131 | n-decyl | ethyl | ethyl | 1 | 0 |
| 132 | n-decyl | ethyl | ethyl | 1 | 1 |
| 133 | n-decyl | ethyl | allyl | 0 | 0 |
| 134 | n-decyl | ethyl | allyl | 1 | 1 |
| 135 | n-octadecyl | ethyl | ethyl | 0 | 0 |
| 136 | n-octadecyl | ethyl | ethyl | 1 | 1 |
| 137 | n-octadecyl | ethyl | allyl | 0 | 0 |
| 138 | n-octadecyl | ethyl | allyl | 1 | 1 |
| 139 | n-octadecyl | n-propyl | ethyl | 0 | 0 |
| 140 | n-octadecyl | n-propyl | ethyl | 1 | 1 |
| 141 | n-octadecyl | n-propyl | allyl | 0 | 0 |
| 142 | n-octadecyl | n-propyl | allyl | 1 | 1 |
| 143 | isopropyl | ethyl | ethyl | 0 | 0 |
| 144 | isopropyl | ethyl | ethyl | 0 | 1 |
| 145 | isopropyl | ethyl | ethyl | 1 | 0 |
| 146 | isopropyl | ethyl | ethyl | 1 | 1 |
| 147 | isopropyl | ethyl | n-propyl | 0 | 0 |
| 148 | isopropyl | ethyl | n-propyl | 1 | 1 |
| 149 | isopropyl | ethyl | allyl | 0 | 0 |
| 150 | isopropyl | ethyl | allyl | 1 | 1 |
| 151 | isopropyl | ethyl | (E)—but-2-en-1-yl | 0 | 0 |
| 152 | isopropyl | ethyl | (E)—but-2-en-1-yl | 0 | 1 |
| 153 | isopropyl | ethyl | (E)—but-2-en-1-yl | 1 | 0 |
| 154 | isopropyl | ethyl | (E)—but-2-en-1-yl | 1 | 1 |
| 155 | isopropyl | ethyl | (E)—1-chloroprop-1-en-3-yl | 0 | 0 |
| 156 | isopropyl | ethyl | (E)—1-chloroprop-1-en-3-yl | 0 | 1 |
| 157 | isopropyl | ethyl | (E)—1-chloroprop-1-en-3-yl | 1 | 0 |
| 158 | isopropyl | ethyl | (E)—1-chloroprop-1-en-3-yl | 1 | 1 |
| 159 | isopropyl | n-propyl | ethyl | 0 | 0 |
| 160 | isopropyl | n-propyl | ethyl | 0 | 1 |
| 161 | isopropyl | n-propyl | ethyl | 1 | 0 |
| 162 | isopropyl | n-propyl | ethyl | 1 | 1 |
| 163 | isopropyl | n-propyl | n-propyl | 0 | 0 |
| 164 | isopropyl | n-propyl | n-propyl | 1 | 1 |
| 165 | isopropyl | n-propyl | allyl | 0 | 0 |
| 166 | isopropyl | n-propyl | allyl | 1 | 1 |
| 167 | isopropyl | n-propyl | (E)—but-2-en-1-yl | 0 | 0 |
| 168 | isopropyl | n-propyl | (E)—but-2-en-1-yl | 0 | 1 |
| 169 | isopropyl | n-propyl | (E)—but-2-en-1-yl | 1 | 0 |
| 170 | isopropyl | n-propyl | (E)—but-2-en-1-yl | 1 | 1 |
| 171 | isopropyl | n-propyl | (E)—1-chloroprop-1-en-3-yl | 0 | 0 |
| 172 | isopropyl | n-propyl | (E)—1-chloroprop-1-en-3-yl | 0 | 1 |
| 173 | isopropyl | n-propyl | (E)—1-chloroprop-1-en-3-yl | 1 | 0 |
| 174 | isopropyl | n-propyl | (E)—1-chloroprop-1-en-3-yl | 1 | 1 |
| 175 | isopropyl | n-propyl | propargyl | 0 | 0 |
| 176 | isopropyl | n-propyl | propargyl | 0 | 1 |
| 177 | isopropyl | n-propyl | propargyl | 1 | 0 |
| 178 | isopropyl | n-propyl | propargyl | 1 | 1 |
| 179 | isopropyl | n-propyl | 2-fluorethyl | 0 | 0 |
| 180 | isopropyl | n-propyl | 2-fluorethyl | 0 | 1 |
| 181 | isopropyl | n-propyl | 2-fluorethyl | 1 | 0 |
| 182 | isopropyl | n-propyl | 2-fluorethyl | 1 | 1 |
| 183 | isopropyl | n-propyl | methoxymethyl | 0 | 0 |
| 184 | isopropyl | n-propyl | methoxymethyl | 0 | 1 |
| 185 | isopropyl | n-propyl | methoxymethyl | 1 | 0 |
| 186 | isopropyl | n-propyl | methoxymethyl | 1 | 1 |
| 187 | isobutyl | ethyl | ethyl | 0 | 0 |
| 188 | isobutyl | ethyl | ethyl | 0 | 1 |
| 189 | isobutyl | ethyl | ethyl | 1 | 0 |
| 190 | isobutyl | ethyl | ethyl | 1 | 1 |
| 191 | isobutyl | n-propyl | ethyl | 0 | 0 |
| 192 | isobutyl | n-propyl | ethyl | 1 | 1 |
| 193 | isobutyl | n-propyl | allyl | 0 | 0 |
| 194 | isobutyl | n-propyl | allyl | 1 | 1 |
| 195 | tert-butyl | ethyl | ethyl | 0 | 0 |
| 196 | tert-butyl | ethyl | ethyl | 1 | 1 |
| 197 | tert-butyl | ethyl | allyl | 0 | 0 |
| 198 | tert-butyl | ethyl | allyl | 1 | 1 |
| 199 | tert-butyl | ethyl | (E)—but-2-en-1-yl | 0 | 0 |

TABLE 1-continued

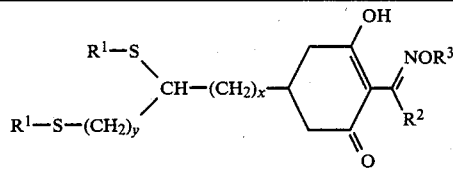

| Compound no. | R¹ | R² | R³ | x | y |
|---|---|---|---|---|---|
| 200 | tert-butyl | ethyl | (E)—but-2-en-1-yl | 0 | 1 |
| 201 | tert-butyl | ethyl | (E)—but-2-en-1-yl | 1 | 0 |
| 202 | tert-butyl | ethyl | (E)—but-2-en-1-yl | 1 | 1 |
| 203 | tert-butyl | ethyl | (E)—1-chloroprop-1-en-3-yl | 0 | 0 |
| 204 | tert-butyl | ethyl | (E)—1-chloroprop-1-en-3-yl | 0 | 1 |
| 205 | tert-butyl | ethyl | (E)—1-chloroprop-1-en-3-yl | 1 | 0 |
| 206 | tert-butyl | ethyl | (E)—1-chloroprop-1-en-3-yl | 1 | 1 |
| 207 | tert-butyl | n-propyl | ethyl | 0 | 0 |
| 208 | tert-butyl | n-propyl | ethyl | 0 | 1 |
| 209 | tert-butyl | n-propyl | ethyl | 1 | 0 |
| 210 | tert-butyl | n-propyl | ethyl | 1 | 1 |
| 211 | tert-butyl | n-propyl | n-propyl | 0 | 0 |
| 212 | tert-butyl | n-propyl | n-propyl | 1 | 1 |
| 213 | tert-butyl | n-propyl | allyl | 0 | 0 |
| 214 | tert-butyl | n-propyl | allyl | 1 | 1 |
| 215 | tert-butyl | n-propyl | (E)—but-2-en-1-yl | 0 | 0 |
| 216 | tert-butyl | n-propyl | (E)—but-2-en-1-yl | 0 | 1 |
| 217 | tert-butyl | n-propyl | (E)—but-2-en-1-yl | 1 | 0 |
| 218 | tert-butyl | n-propyl | (E)—but-2-en-1-yl | 1 | 1 |
| 219 | tert-butyl | n-propyl | (E)—1-chloroprop-1-en-3-yl | 0 | 0 |
| 220 | tert-butyl | n-propyl | (E)—1-chloroprop-1-en-3-yl | 0 | 1 |
| 221 | tert-butyl | n-propyl | (E)—1-chloroprop-1-en-3-yl | 1 | 0 |
| 222 | tert-butyl | n-propyl | (E)—1-chloroprop-1-en-3-yl | 1 | 1 |
| 223 | allyl | ethyl | ethyl | 0 | 0 |
| 224 | allyl | ethyl | ethyl | 0 | 1 |
| 225 | allyl | ethyl | ethyl | 1 | 0 |
| 226 | allyl | ethyl | ethyl | 1 | 1 |
| 227 | allyl | ethyl | n-propyl | 0 | 0 |
| 228 | allyl | ethyl | n-propyl | 1 | 1 |
| 229 | allyl | ethyl | allyl | 0 | 0 |
| 230 | allyl | ethyl | allyl | 1 | 1 |
| 231 | allyl | ethyl | (E)—but-2-en-1-yl | 0 | 0 |
| 232 | allyl | ethyl | (E)—but-2-en-1-yl | 0 | 1 |
| 233 | allyl | ethyl | (E)—but-2-en-1-yl | 1 | 0 |
| 234 | allyl | ethyl | (E)—but-2-en-1-yl | 1 | 1 |
| 235 | allyl | ethyl | (E)—1-chloroprop-1-en-3-yl | 0 | 0 |
| 236 | allyl | ethyl | (E)—1-chloroprop-1-en-3-yl | 0 | 1 |
| 237 | allyl | ethyl | (E)—1-chloroprop-1-en-3-yl | 1 | 0 |
| 238 | allyl | ethyl | (E)—1-chloroprop-1-en-3-yl | 1 | 1 |
| 239 | allyl | ethyl | propargyl | 0 | 0 |
| 240 | allyl | ethyl | propargyl | 0 | 1 |
| 241 | allyl | ethyl | propargyl | 1 | 0 |
| 242 | allyl | ethyl | propargyl | 1 | 1 |
| 243 | allyl | ethyl | 2-fluorethyl | 0 | 0 |
| 244 | allyl | ethyl | 2-fluorethyl | 0 | 1 |
| 245 | allyl | ethyl | 2-fluorethyl | 1 | 0 |
| 246 | allyl | ethyl | 2-fluorethyl | 1 | 1 |
| 247 | allyl | ethyl | methoxymethyl | 0 | 0 |
| 248 | allyl | ethyl | methoxymethyl | 0 | 1 |
| 249 | allyl | ethyl | methoxymethyl | 1 | 0 |
| 250 | allyl | ethyl | methoxymethyl | 1 | 1 |
| 251 | allyl | n-propyl | ethyl | 0 | 0 |
| 252 | allyl | n-propyl | ethyl | 0 | 1 |
| 253 | allyl | n-propyl | ethyl | 1 | 0 |
| 254 | allyl | n-propyl | ethyl | 1 | 1 |
| 255 | allyl | n-propyl | n-propyl | 0 | 0 |
| 256 | allyl | n-propyl | n-propyl | 1 | 1 |
| 257 | allyl | n-propyl | allyl | 0 | 0 |
| 258 | allyl | n-propyl | allyl | 1 | 1 |
| 259 | allyl | n-propyl | (E)—but-2-en-1-yl | 0 | 0 |
| 260 | allyl | n-propyl | (E)—but-2-en-1-yl | 0 | 1 |
| 261 | allyl | n-propyl | (E)—but-2-en-1-yl | 1 | 0 |
| 262 | allyl | n-propyl | (E)—but-2-en-1-yl | 1 | 1 |
| 263 | allyl | n-propyl | (E)—1-chloroprop-1-en-3-yl | 0 | 0 |
| 264 | allyl | n-propyl | (E)—1-chloroprop-1-en-3-yl | 0 | 1 |
| 265 | allyl | n-propyl | (E)—1-chloroprop-1-en-3-yl | 1 | 0 |
| 266 | 2-methyl-prop-2-en-1-yl | ethyl | ethyl | 0 | 0 |
| 267 | 2-methyl-prop-2-en-1-yl | ethyl | ethyl | 1 | 1 |
| 268 | 2-methyl-prop-2-en-1-yl | ethyl | allyl | 0 | 0 |
| 269 | 2-methyl-prop-2-en-1-yl | ethyl | allyl | 1 | 1 |
| 270 | 2-methyl-prop-2-en-1-yl | n-propyl | ethyl | 0 | 0 |

TABLE 1-continued

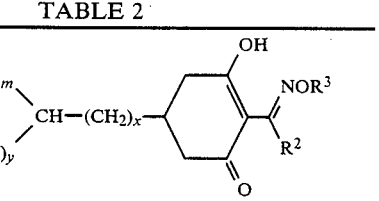

| Compound no. | R¹ | R² | R³ | x | y |
|---|---|---|---|---|---|
| 271 | 2-methyl-prop-2-en-1-yl | n-propyl | ethyl | 1 | 1 |
| 272 | 2-methyl-prop-2-en-1-yl | n-propyl | allyl | 0 | 0 |
| 273 | 2-methyl-prop-2-en-1-yl | n-propyl | allyl | 1 | 1 |
| 274 | 2-methoxyethyl | ethyl | ethyl | 0 | 0 |
| 275 | 2-methoxyethyl | ethyl | ethyl | 1 | 1 |
| 276 | 2-methoxyethyl | ethyl | allyl | 0 | 0 |
| 277 | 2-methoxyethyl | ethyl | allyl | 1 | 1 |
| 278 | 2-methoxyethyl | n-propyl | ethyl | 0 | 0 |
| 279 | 2-methoxyethyl | n-propyl | ethyl | 0 | 1 |
| 280 | 2-methoxyethyl | n-propyl | ethyl | 1 | 0 |
| 281 | 2-methoxyethyl | n-propyl | ethyl | 1 | 1 |
| 282 | 2-methoxyethyl | n-propyl | n-propyl | 0 | 0 |
| 283 | 2-methoxyethyl | n-propyl | n-propyl | 1 | 1 |
| 284 | 2-methoxyethyl | n-propyl | allyl | 0 | 0 |
| 285 | 2-methoxyethyl | n-propyl | allyl | 1 | 1 |
| 286 | 2-methoxyethyl | n-propyl | (E)—but-2-en-1-yl | 0 | 0 |
| 287 | 2-methoxyethyl | n-propyl | (E)—but-2-en-1-yl | 0 | 1 |
| 288 | 2-methoxyethyl | n-propyl | (E)—but-2-en-1-yl | 1 | 0 |
| 289 | 2-methoxyethyl | n-propyl | (E)—but-2-en-1-yl | 1 | 1 |
| 290 | 2-methoxyethyl | n-propyl | (E)—1-chloroprop-1-en-3-yl | 0 | 0 |
| 291 | 2-methoxyethyl | n-propyl | (E)—1-chloroprop-1-en-3-yl | 0 | 1 |
| 292 | 2-methoxyethyl | n-propyl | (E)—1-chloroprop-1-en-3-yl | 1 | 0 |
| 293 | 2-methoxyethyl | n-propyl | (E)—1-chloroprop-1-en-3-yl | 1 | 1 |
| 294 | 2-methoxyethyl | n-propyl | 1,1,2-trichloroprop-1-en-3-yl | 0 | 0 |
| 295 | 2-methoxyethyl | n-propyl | 1,1,2-trichloroprop-1-en-3-yl | 1 | 0 |
| 296 | 2-methoxyethyl | n-propyl | 1,1,2-trichloroprop-1-en-3-yl | 1 | 1 |
| 297 | 2-methoxyethyl | n-propyl | propargyl | 0 | 0 |
| 298 | 2-methoxyethyl | n-propyl | propargyl | 1 | 1 |
| 299 | 2-(N,N—dimethylamino)eth-1-yl | ethyl | ethyl | 0 | 0 |
| 300 | 2-(N,N—dimethylamino)eth-1-yl | ethyl | ethyl | 1 | 1 |
| 301 | 2-(N,N—dimethylamino)eth-1-yl | ethyl | allyl | 0 | 0 |
| 302 | 2-(N,N—dimethylamino)eth-1-yl | ethyl | allyl | 1 | 1 |

TABLE 2

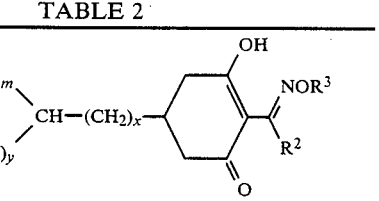

| Compound no. | R¹ | R² | R³ | x | y | m | n |
|---|---|---|---|---|---|---|---|
| 303 | methyl | n-propyl | ethyl | 0 | 0 | 1 | 0 |
| 304 | methyl | n-propyl | ethyl | 0 | 0 | 2 | 2 |
| 305 | ethyl | ethyl | ethyl | 0 | 0 | 1 | 0 |
| 306 | ethyl | ethyl | ethyl | 0 | 0 | 2 | 1 |
| 307 | ethyl | ethyl | ethyl | 0 | 0 | 2 | 2 |
| 308 | ethyl | n-propyl | ethyl | 0 | 0 | 1 | 0 |
| 309 | ethyl | n-propyl | ethyl | 0 | 0 | 2 | 2 |
| 310 | ethyl | n-propyl | allyl | 0 | 0 | 1 | 0 |
| 311 | ethyl | n-propyl | (E)—1-chloroprop-1-en-3-yl | 0 | 0 | 1 | 0 |
| 312 | ethyl | n-propyl | (E)—but-2-en-1-yl | 0 | 0 | 1 | 0 |
| 313 | ethyl | n-propyl | ethyl | 1 | 1 | 1 | 0 |
| 314 | ethyl | n-propyl | ethyl | 1 | 1 | 2 | 2 |
| 315 | ethyl | n-propyl | (E)—-chloroprop-1-en-3-yl | 1 | 1 | 1 | 0 |
| 316 | ethyl | n-propyl | (E)—-chloroprop-1-en-3-yl | 1 | 1 | 2 | 2 |

TABLE 3

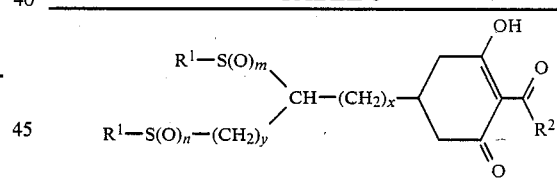

| Compound no. | R¹ | R² | x | y | m | n |
|---|---|---|---|---|---|---|
| 317 | methyl | ethyl | 0 | 0 | 0 | 0 |
| 318 | methyl | ethyl | 0 | 0 | 1 | 0 |
| 319 | methyl | ethyl | 0 | 0 | 2 | 2 |
| 320 | ethyl | ethyl | 0 | 0 | 0 | 0 |
| 321 | ethyl | ethyl | 0 | 0 | 1 | 0 |
| 322 | ethyl | ethyl | 0 | 0 | 2 | 2 |
| 323 | ethyl | ethyl | 1 | 1 | 0 | 0 |
| 324 | ethyl | ethyl | 1 | 1 | 1 | 0 |
| 325 | ethyl | ethyl | 1 | 1 | 2 | 2 |
| 326 | ethyl | n-propyl | 0 | 0 | 0 | 0 |
| 327 | ethyl | n-propyl | 0 | 0 | 1 | 0 |
| 328 | ethyl | n-propyl | 0 | 0 | 2 | 2 |
| 329 | ethyl | n-propyl | 1 | 1 | 0 | 0 |
| 330 | ethyl | n-propyl | 1 | 1 | 1 | 0 |
| 331 | ethyl | n-propyl | 1 | 1 | 2 | 2 |
| 332 | n-propyl | n-propyl | 0 | 0 | 0 | 0 |
| 333 | n-butyl | ethyl | 0 | 0 | 0 | 0 |
| 352 | ethyl | methyl | 0 | 0 | 0 | 0 |
| 353 | ethyl | n-butyl | 0 | 0 | 0 | 0 |
| 334 | n-pentyl | ethyl | 0 | 0 | 0 | 0 |
| 335 | n-decyl | ethyl | 0 | 0 | 0 | 0 |
| 336 | n-octadecyl | ethyl | 0 | 0 | 0 | 0 |

TABLE 3-continued $$R^1-S(O)_m \diagdown CH-(CH_2)_x- \text{[cyclohexenone with OH, R}^2\text{, =O]}$$
$$R^1-S(O)_n-(CH_2)_y \diagup$$

| Compound no. | R¹ | R² | x | y | m | n |
|---|---|---|---|---|---|---|
| 337 | isopropyl | n-propyl | 0 | 0 | 0 | 0 |
| 338 | tert.-butyl | n-propyl | 0 | 0 | 0 | 0 |
| 339 | allyl | n-propyl | 0 | 0 | 0 | 0 |
| 340 | allyl | n-propyl | 1 | 1 | 0 | 0 |
| 341 | 2-methoxyethyl | n-propyl | 0 | 0 | 0 | 0 |
| 342 | 2-methoxyethyl | n-propyl | 1 | 1 | 0 | 0 |
| 343 | 2-(N,N—dimethylamino)eth-1-yl | ethyl | 0 | 0 | 0 | 0 |
| 344 | 2-(N,N—dimethylamino)eth-1-yl | ethyl | 1 | 1 | 0 | 0 |

TABLE 4

Examples of salts of the active ingredients given in TABLES 1 to 3:

| Compound no. | Structure (cf. comp. no.) | Type of salt | M.p. (°C.) |
|---|---|---|---|
| 345 | 57 | sodium | |
| 346 | 57 | barium | |
| 347 | 57 | copper (II) | |
| 348 | 57 | tri-n-butylammonium | |
| 349 | 57 | benzyl-trimethylammonium | |
| 350 | 57 | trimethylsulfoxonium | |

The compounds of the formula I are identified and characterized most easily with the aid of proton nuclear resonance spectroscopy. In Table 5 below, some ¹H-NMR data specific to structure are given (solvent: CDCl₃; t =triplet, q =quartet, m =multiplet).

TABLE 5

| Compound no. | Characteristic ¹H-NMR-data( ) in ppm |
|---|---|
| 1 | 1.15 (t); 2.15 (s); 4.12 (q) |
| 37 | 1.28 (m); 2.39 (s); 4.11 (q) |
| 40 | 1.17 (t); 1.27 (t); 1.32 (t); 3.73 (d); 4.10 (q) |
| 42 | 0.98 (t); 1.13 (t); 1.27 (t); 3.73 (d); 4.20 (t) |
| 44 | 1.13 (t); 1.27 (t); 3.72 (d); 4.54 (d); 5.98 (m) |
| 48 | 1.15 (t); 1.28 (t); 1.78 (d); 3.73 (d); 4.44 (d); 5.62 (m); 5.83 (m) |
| 52 | 1.14 (t); 1.28 (t); 3.73 (d); 4.51 (d); 6.10 (m); 6.35 (d) |
| 56 | 1.14 (t), 1.27 (t); 3.74 (d); 4.66 (s) |
| 57 | 0.98 (t); 1.26 (t); 1.32 (t); 3.72 (d); 4.09 (q) |
| 60 | 0.98 (t); 1.24 (t); 1.30 (t); 4.10 (q) |
| 61 | 0.98 (t); 1.28 (t); 3.73 (d); 4.52 (d); 5.97 (m) |
| 63 | 0.97 (t); 1.28 (t); 3.73 (d); 4.30 (s) |
| 65 | 0.96 (t); 1.27 (t); 3.73 (d); 4.88 (s) |
| 66 | 0.95 (t); 1.26 (t); 3.71 (d); 3.86 (s) |
| 67 | 0.97 (t); 1.27 (t); 3.71 (d); 4.00 (t) |
| 71 | 0.96 (t); 1.27 (t); 3.71 (d); 4.43 (d) |
| 75 | 0.98 (t); 1.27 (t); 3.72 (d); 4.52 (d); 6.08 (m); 6.33 (d); |
| 79 | 0.96 (t); 2.48 (s), 3.72 (d); 4.64 (s) |
| 80 | 0.96 (t); 3.43 (s); 3.72 (d); 5.05 (s) |
| 98 | 0.99 (m); 2.0–3.0 (m); 4.10 (q) |
| 159 | 0.97 (t); 1.32 (m); 4.10 (q) |
| 207 | 0.97 (t); 1.37 (s); 4.09 (q) |
| 219 | 0.95 (t); 1.37 (s); 4.51 (d) |
| 309 | 0.98 (t); 1.43 (t); 4.10 (q) |
| 317 | 0.88 (t); 2.15 (s); 3.57 (s) |
| 320 | 1.12 (t); 1.27 (t); 3.05 (q); 3.77 (d) |
| 326 | 0.97 (t); 1.27 (t); 3.00 (t); 3.75 (d) |
| 328 | 0.97 (t); 1.43 (t); 2.7–3.7 (m) |
| 329 | 0.98 (t); 1.28 (t); 2.1–3.3 (m) |
| 332 | 0.97 (m); 1.63 (m); 2.0–3.1 (m) |

TABLE 5-continued

| Compound no. | Characteristic ¹H-NMR-data( ) in ppm |
|---|---|
| 337 | 0.97 (t); 1.28 (m); 3.82 (d) |
| 338 | 0.98 (t); 1.37 (s); 3.95 (s) |
| 351 | 0.92 (t); 3.73 (d); 4.10 (q) |
| 352 | 1.28 (t); 2.4–3.0 (m); 3.76 (d) |
| 353 | 0.92 (t); 1.27 (t); 3.74 (d) |

The cyclohexenone derivatives of the formula I may be applied for instance in the form of directly sprayable solutions, powders, suspensions (including high-percentage aqueous, oily or other suspensions), dispersions, emulsions, oil dispersions, pastes, dusts, broadcasting agents or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, and paraffin, tetrahydrocarbons such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenizesd in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonate, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols and octadecanols, salts of sulfated fatty alcohol glycol ethers, condensation products of sulfonated naphthalene and naphthalene derivatives with formaldehyde, condensation products of naphthalene or naphthalenesulfonic acids with phenol or formaldehyde, polyoxyethylene octylphenol ethers, ethoxylated isooctyl phenol, ethoxylated octylphenol and ethyoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate and ureas, and vegetable products such as grain flours, bark meal, wood meal and nutshell meal, cellulosic powders, etc.

The formulations contain from 0.1 to 95, and preferably from 0.5 to 90, % by weight of active ingredient.

Examples of formulations are given below.

I. 90 parts of compound no. 60 is mixed with 10 parts by weight of N-methyl-α-pyrrolidone. A mixture is obtained which is suitable for application in the form of very fine drops.

II. 20 parts by weight of compound no. 61 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of active ingredient.

III. 20 parts by weight of compound no. 320 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of active ingredient.

IV. 20 parts by weight of compound no. 52 is dissolved in a mixture consisting of 25 parts by weight of cyclohexanone, 65 parts by weight of a mineral oil fraction having a boiling point between 210 and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of active ingredient.

V. 20 parts by weight of compound no. 44 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of active ingredient.

VI. 3 parts by weight of compound no. 40 is intimately mixed with 97 parts by weight of particulate kaolin. A dust is obtained containing 3% by weight of active ingredient.

VII. 30 parts by weight of compound no. 48 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by compound no. 75 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

IX. 40 parts by weight of compound no. 57 is dissolved in 60 parts by weight of a mixture consisting of 93wt% of xylene and 7wt% of the adduct of 8 moles of ethylene oxide and 1 mole of nonylphenol. A solution is obtained containing 40wt% of the active ingredient.

The novel cyclohexenone derivatives of the formula I in which A is NOR$^3$ have a good herbicidal action, particularly on species from the Gramineae family. They are tolerated by, and are thus selective in, broad-leaved crops and monocotyledons not belonging to the Gramineae. Some of the novel compounds are suitable for combating unwanted grasses in cereals.

The active ingredients, or agents containing them, may be applied pre- or post-emergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amounts of active ingredient applied depends on the time of the year, the plants to be combated and their growth stage, and varies from 0.03 to 3 kg/ha, but is preferably from 0.06 to 1.0 kg/ha.

The action of the cyclohexenone derivatives of the formula I (A =NOR$^3$) on plant growth is demonstrated in greenhouse experiments.

The vessels employed were plastic flowerpots having a volume of 300 cm$^3$, and which were filled with a sandy loam containing about 3.0% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germin-ation and growth. Transparent plastic covers were then placed on the vessels until the plants had taken root. The cover ensured uniform germin-ation of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. The application rates for postemergence treatment were 0.25 and 0.5 kg of active ingredient per hectare. No covers were placed on the vessels in this method.

The pots were set up in the greenhousespecies from warmer areas at from 20° C. to 35° C., and species from moderate climates at 10 to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the greenhouse experiments were as follows: Alopecurus myosuroides, Avena fatua, Avena sativa, Beta vulgaris, Digitaria sanguinalis, Echinochloa crus-galli, Lolium multiflorum, Medicago sativa, Setaria italica, Sinapis alba, Triticum aestivum and Zea mays.

On postemergence application of 3 kg/ha, compounds nos. 60, 61, 75, 52, 44, 40 and 48 selected by way of example provided to be herbicidally effective on plants from the Gramineae family. The growth of mustard, selected as an example of a broadleaved crop plant, was hardly impaired, if at all.

Volunteer Indian corn and unwanted grassy species are well combated with postemergence applications of, for instance, compound no. 57, no damage being caused to the broadleaved crop plant sugarbeets.

To combat grassy vegetation in alfalfa, for example compounds nos. 60, 61 and 75 may be used postemergence. The active ingredients have no effect on the crop plants; they are selective.

The cyclohexenone derivatives of the formula I (A =NOR$^3$) may also be used as grass herbicides in a graminaceous crop such a wheat. Compounds nos. 60, 61 and 75 selected by way of example are suitable for combating important grassy weeds postemergence; the wheat plants suffer hardly any damage, if at all.

In view of the spectrum of weeds which can be combated, the tolerance of the active ingredients according to the invention by crop plants, the desired influence on the growth of crop plants, and in view of the numerous application methods possible, the compounds according to the invention may be used in a large number of crop plants.

The following crops may be mentioned by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | bermudagrass |
| Daucus carota | carrots |
| Elaeis guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactua sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicis faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the cyclohexenone derivatives of the formula I (A =NOR$^3$) may be mixed and applied together with numerous representatives of other herbicidal or growth-regulating active ingredient groups. Examples or suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acid derivatives, etc.

It may also be useful to apply the cyclohexenone derivatives of the formula I (A =NOR$^3$), either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

The cyclohexenone derivatives of the formula I (A =oxygen) may have a variety of influences on practically all plant development stages, and may therefore be used as growth regulators. The diversity of action of growth regulators depends especially on (a) the type and variety of plant;
(b) the time applied, with reference to the development stage of the plants and the time of the year;
(c) the place and method of application (seed treatment, soil treatment, or application to foliage);
(d) climatic factors, e.g., temperature, amount of precipitate, day length and light intensity;
(e) soil conditions (including fertilization);
(f) the formulation of the active ingredient; and
(g) the concentration at which the active ingredient is applied.

A description of some of the various possibilities of using the growth regulators according to the invention in agriculture and horticulture is given below.

A. Vegetable plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated inplants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and - because of the relatively low leaf or plant mass - attack by various (especially fungus) diseases. The inhibition of vegetative growth also makes closer planting possible in numerous crops, which means an increase in yield, based on the area cropped.

B. Better yields both of plant parts and plant materials may be obtained with the active ingredients according to the invention. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The cyclohexenone derivatives of the formula I (A =oxygen) may raise the yield by influencing plant metabolism or by promoting or inhibiting vegetative and-/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia, the size of the stomata opening is reduced;
a thicker epidermis and cuticle are formed;
penetration of the soil by the roots is improved;
the micro-climate in the stand is favorably influenced by the more compact growth.

The active ingredients of the formula I to be used in accordance with the invention (A =oxygen) may be applied not only to the seed (as a disinfectant), but also to the soil, i.e., via the roots, and—the method particularly preferred—to the foliage by spraying.

As a result of the good crop plant tolerance, the application rate may vary considerably. When seed is treated, active ingredient amounts of from 0.001 to 50, and preferably from 0.01 to 10, g per kg of seed are generally needed. When the soil or foliage is treated, rates of from 0.01 to 10, and preferably from 0.05 to 3, kg per hectare are generally considered to be sufficient.

To determine the growth-regulating properties of the candidate compounds, a culture medium was supplied with sufficient nutrients, and test plants were grown therein in plastic pots approx. 12.5 cm in diameter.

The candidate compounds were sprayed as aqueous formulations onto the plants. The growth-regulating action observed was confirmed at the end of the experiment by measuring the growth height. The figures obtained were compared with those for untreated plants. Chlorocholine chloride was used for comparison purposes.

Compounds nos. 320, 337, 352 and 353 selected by way of example exhibited favorable growth-regulating properties for example in spring wheat, spring barley and sunflowers.

Not only was growth height reduced - the leaves also took on a more intense color. The increased chlorophyll content is indicative of a higher rate of photosynthesis, making for bigger yields.

Young rice seedlings (Girona variety) were cultivated in a nutrient solution containing various concentrations of the candidate compounds. After 6 days' treatment at 25° C. in continuous light, the active ingredient concentration was determined which decreased lengthwise growth of the second leaf-sheath by 50% (cf. W. Rademacher and J. Jung, Berichte aus dem Fachgebiet Herbologie, issue no. 4, pp. 127-134, Hohenheim University, 1983).

Compound no. 320, for example, exhibited favorable growth-regulating properties in this experiment.

In these application forms, the novel agents of the formula I (A =oxygen) may be present with other active ingredients, e.g., herbicides, insecticides, other growth regulators and fungicides, and also admixed and applied together with fertilizers. When the compounds according to the invention are mixed with other growth regulators, synergistic effects may also occur, i.e., the effectiveness of the combination is greater than that of the added effects of its individual components.

We claim:

1. Cyclohexenone derivatives of the formula I

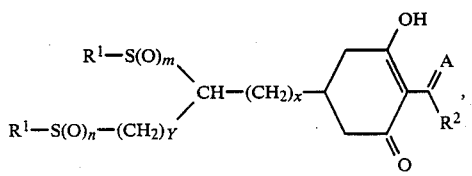

where $R^1$ is $C_1$-$C_{18}$-alkyl, $C_3$-$C_6$-alkoxyalkyl, $C_3$-$C_6$alkylthioalkyl, $C_3$-$C_6$-dialkylaminoalkyl, $C_3$-$C_6$-alkenyl or $C_3$-$C_6$-alkynyl, $R^2$ is $C_1$-$C_4$-alkyl, A is oxygen or $NOR^3$, $R^3$ denoting $C_1$-$C_4$-alkyl, $C_3$-$C_4$-alkenyl, $C_3$-$C_4$-alkynyl, $C_2$-$C_4$-haloalkyl, $C_2$-$C_4$-haloalkenyl or $C_2$-$C_4$-alkoxyalkyl, m and n are identical or different and each denotes 0, 1 or 2, and x and y are identical or different and each denotes 0 or 1, and salts thereof.

2. A cyclohexenone derivative of the formula I as set forth in claim 1, where m, n, x and y are each 0 and A is $NOR^3$.

3. A compound of the formula I as set forth in claim 1, where $R^1$ is ethyl, $R^2$ is n-propyl, A is $NOR^3$, $R^3$ is ethyl, allyl or 1-chloroprop-1-en-3-yl, x is 0 or 1, y is 0 or 1 and n is 0.

4. A herbicide containing an inert carrier and a cyclohexenone derivative of the formula

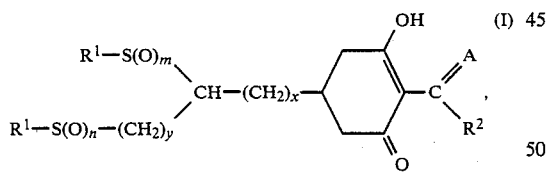

where $R^1$ is $C_1$-$C_{18}$-alkyl, $C_3$-$C_6$-alkoxyalkyl, $C_3$-$C_6$-alkylthioalkyl, $C_3$-$C_6$-dialkylaminoalkyl, $C_3$-$C_6$-alkenyl or $C_3$-$C_6$-alkynyl, $R^2$ is $C_1$-$C_4$-alkyl, A is $NOR^3$, $R^3$ denoting $C_1$-$C_4$alkyl, $C_3$-$C_4$alkenyl, $C_3$-$C_4$-alkynyl, $C_2$-$C_4$-haloalkyl, $C_2$-$C_4$-haloalkenyl or $C_2$-$C_4$-alkoxyalkyl, m and n are identical or different and each denotes 0, 1 or 2, and x and y are identical or different and each denotes 0 or 1, or a salt thereof.

5. A process for combating the growth of unwanted plants, wherein the unwanted plants or the area to be kept free from unwanted plant growth are treated with a herbicidally effective amount of a cyclohexenone derivative of the formula

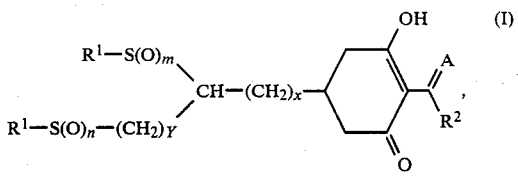

where $R^1$ is $C_1$-$C_{18}$-alkyl, $C_3$-$C_6$-alkoxyalkyl, $C_3$-$C_6$-alkylthioalkyl, $C_3$-$C_6$-dialkylaminoalkyl, $C_3$-$C_6$-alkenyl or $C_3$-$C_6$-alkynyl, $R^2$ is $C_1$-$C_4$-alkyl, A is $NOR^3$, $R^3$ denoting $C_1$-$C_4$-alkyl, $C_3$-$C_4$-alkenyl, $C_3$-$C_4$-alkynyl, $C_2$-$C_4$-haloalkyl, $C_2$-$C_4$-haloalkenyl or $C_2$-$C_4$-alkoxyalkyl, m and n are identical or different and each denotes 0, 1 or 2, and x and y are identical or different and each denotes 0 or 1, or a salt thereof.

6. An agent for regulating plant growth, containing an inert additive and a cyclohexenone derivative of the formula

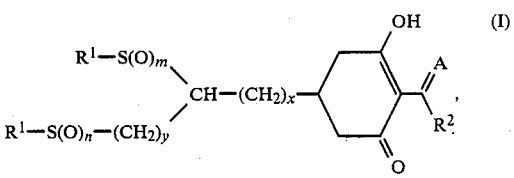

where $R^1$ is $C_1$-$C_{18}$-alkyl, $C_3$-$C_6$-alkoxyalkyl, $C_3$-$C_6$-alkylthioalkyl, $C_3$-$C_6$-dialkylaminoalkyl, $C_3$-$C_6$-alkenyl or $C_3$-$C_6$-alkynyl, $R^2$ is $C_1$-$C_4$-alkyl, A is oxygen, m and n are identical or different and each denotes 0, 1 or 2, and x and y are identical or different and each denotes 0 or 1, or a salt thereof.

7. A process for regulating plant growth, wherein an effective amount of a cyclohexenone derivative of the formula

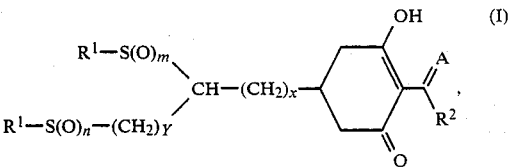

where $R^1$ is $C_1$-$C_{18}$-alkyl, $C_3$-$C_6$-alkoxyalkyl, $C_3$-$C_6$-alkylthioalkyl, $C_3$-$C_6$-dialkylaminoalkyl, $C_3$-$C_6$-alkenyl or $C_3$-$C_6$-alkynyl, $R^2$ is $C_1$-$C_4$-alkyl, A is oxygen, m and n are identical or different and each denotes 0, 1 or 2, and x and y are identical or different and each denotes 0 or 1, or of a salt thereof, is allowed to act on plants or their habitat.

8. A cyclohexenone derivative of the formula I as set forth in claim 1, wherein m, n, x and y are O, A is $NOR^3$, $R^2$ is n-propyl and $R^3$ is ethyl, allyl or 1-chloroprop-1-en-3-yl.

* * * * *